United States Patent [19]

Uematsu et al.

[11] Patent Number: 4,519,890
[45] Date of Patent: May 28, 1985

[54] FLOW SYSTEM GLASS ELECTRODE

[75] Inventors: Hiroaki Uematsu; Junji Aoki; Narihiro Oku, all of Kyoto, Japan

[73] Assignee: Horiba, Ltd., Kyoto, Japan

[21] Appl. No.: 614,225

[22] Filed: May 24, 1984

[30] Foreign Application Priority Data

Jun. 7, 1983 [JP] Japan ............................ 58-87294[U]

[51] Int. Cl.³ ............................................ G01N 27/36
[52] U.S. Cl. ..................................... 204/409; 204/420
[58] Field of Search ....................... 204/420, 409, 1 H; 128/635; 324/438, 425

[56] References Cited

U.S. PATENT DOCUMENTS

| | | | |
|---|---|---|---|
| 3,700,577 | 10/1972 | Grauer | 204/420 |
| 3,840,438 | 10/1974 | Ast et al. | 204/420 X |
| 3,853,732 | 12/1974 | Brand et al. | 204/420 X |
| 3,926,765 | 12/1975 | Haddad | 204/420 |
| 4,149,950 | 4/1979 | Potts | 204/420 X |
| 4,233,136 | 11/1980 | Spaziani et al. | 204/409 |

FOREIGN PATENT DOCUMENTS 3010461 10/1981 Fed. Rep. of Germany ...... 204/420
3010470 10/1981 Fed. Rep. of Germany ...... 204/420

Primary Examiner—G. L. Kaplan
Attorney, Agent, or Firm—Wenderoth, Lind & Ponack

[57] ABSTRACT

A flow system glass electrode in use for pH measurement, which houses the glass electrode body in a resin block to improve an impact resistance, the glass electrode body being sealed by a packing to be small-sized and improve the degree of freedom in the direction of the use, sample flow tubes each being equal in an inner diameter to a response film and separate from the glass electrode body in order to eliminate stagnation of a sample liquid, enable the measurement of a minute sample, and facilitate manufacture and assembly of the electrode, the sample flow tubes being connected with a liquid inlet and a liquid outlet at the glass electrode body through couplings respectively.

3 Claims, 3 Drawing Figures

FLOW SYSTEM GLASS ELECTRODE

BACKGROUND OF THE INVENTION

1. Field of the Invention

This invention relates to a glass electrode, and more particularly to a flow system glass electrode.

2. Description of the Prior Art

This kind of glass electrode, which has hitherto been used, includes those as shown in FIGS. 1 and 2, which are both glass-sealed so that air (a) cannot completely be exhausted from the electrode from the manufacture technical point, whereby the glass electrode itself becomes larger, and when it is kept upright or laid down, the air comes into contact with the inner electrode (b) or response film (c), thereby creating the problem in that the measurement in such state is impossible and the handling of the electrode is inconvenient. In addition, there has been a defect of being breakable due to exposure of glass electrode body to the exterior.

SUMMARY OF THE INVENTION

An object of the invention is to provide a flow system glass electrode not breakable, small-sized, not-limited in the use, and measurable of a minute sample, thereby being of high value-in-use and aiming at elimination of the conventional defects.

This invention is characterized in that the flow system glass electrode houses into a resin block to flow system glass electrode body which is provided with a response film along the internal flow conduit and seals an internal electrode and liquid with a packing, sample flow tubes at the entrance and exit side equal in inner diameter to the response film are inserted through the resin block walls, the sample flow tubes and a liquid inlet and a liquid outlet at the glass electrode body are connected with each other through couplings, and the space in the resin block except for the glass electrode body is filled with a filler of electrical insulating property.

In other words, the flow system glass electrode of the invention, which contains the body in the resin block filled with the filler, is not broken even when abutting against a foreign object, thereby being extremely high in impact resistance.

Also, since the glass electrode body is sealed with the packing, an amount of air entering into the body is extremely reducible. Therefore, the direction of the use is not limited, so that the electrode is usable in high degree of freedom and the body itself can be miniaturized. Such miniaturization thereof leads to the use of small-sized resin block, thereby enabling miniaturization of the electrode as a whole.

Furthermore, the sample flow tubes inserted into the resin block each are equal in inner diameter to the response film at the glass electrode body, the flow tubes connecting with the liquid outlet and liquid inlet at the glass electrode body, thereby enabling the sample flow tubes to be made linear so as to be free from stagnation of the sample. Although the flow system glass electrode is measurable of a minute sample in comparison with the dipping type one, the invention as abovementioned devices the straight line formation to eliminate the stagnation, thereby further enabling the measurement of minute sample.

Also, the sample flow conduit is formed in the straight line by connecting the sample flow tubes inserted into the resin block with the liquid outlet and inlet at the glass electrode body side, thereby facilitating construction and assembly of electrode. In other words, since there is no need of using glass material generally for the sample flow tubes separate from the glass electrode body, it is easy to manufacture the sample flow tubes each equal in inner diameter to the response film and also the sample flow tubes, when separate from the glass electrode body, are easy to assemble in the reasonable procedure.

There is a preferred embodiment of the flow system glass electrode of the invention, which includes the sample flow tubes constituted of polytetrafluoroethylene. Since such polytetrafluoroethylene is superior in workability, the sample flow tubes each equal in inner diameter to the response film are producible with ease and accuracy.

There is a modified embodiment of the invention which is constituted of a glass electrode body, resin block, sample flow tubes, couplings and filler, which are all transparent. Hence, the flow state of sample liquid within the electrode is recognizable with ease by external vision. For example, stagnation, even when created, is simply discoverable.

The above and further objects and novel features of the invention will become apparent from the following description with reference to the accompanying drawings.

DESCRIPTION OF THE PREFERRED EMBODIMENTS

Figure 1:
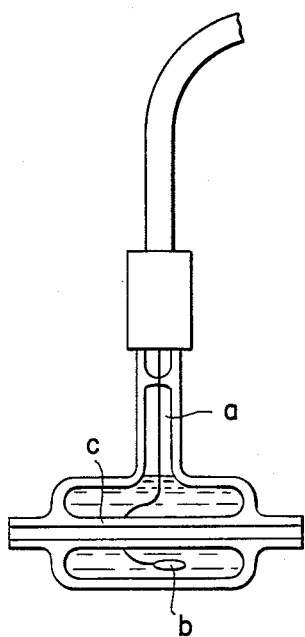
FIGS. 1 and 2 are sectional views of conventional flow system glass electrodes.
Figure 2:
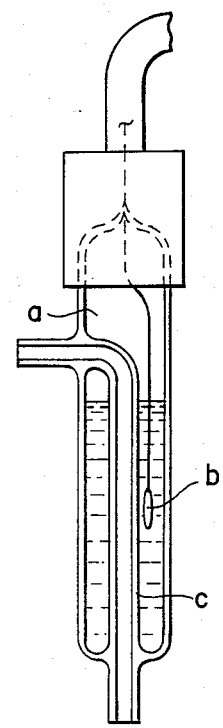
Figure 3:
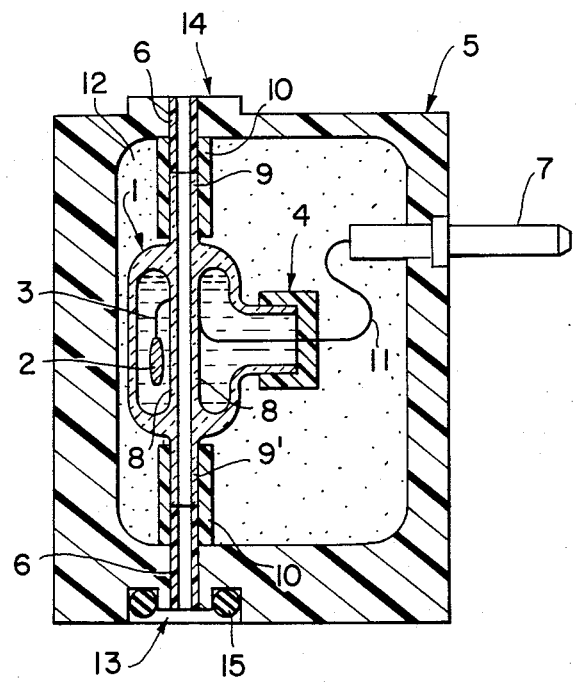
FIG. 3 is a sectional view of an embodiment of a flow system glass electrode of the invention.

Referring to FIG. 3, reference numeral 1 designates a flow system glass electrode body, which is provided with a response film 8 along an internal flow conduit and has an internal electrode and internal liquid, sealed with a packing 4. Although the conventional electrodes shown in FIGS. 1 and 2 are sealed by glass, the electrode of the invention sealed with the packing 4 is extremely reducible of air to be taken into the electrode. Hence, even when the electrode is either upright or laid down, no air contacts with the internal electrode 2, thereby raising the degree of freedom in the direction of the use. Although the electrode glass-sealed is bulky and large-sized at the sealing portion, including volume of mixed air, the same sealed with the packing can be small-sized.

In FIG. 3, reference numeral 5 designates a resin block comprising a box of resin and a lid of resin of tight-closed construction, into which the flow system glass electrode body 1 is contained. The block 5 is preferable to be formed of transparent resin, such as acrylic. The reason for the above is that the flow condition, such as stagnation, of sample liquid within the electrode is recognizable with each directly by vision from the exterior. From this viewpoint, it is desirable that the glass electrode body 1 is formed of a transparent glass material and also the sample flow tubes and couplings to be discussed below are formed of the same material. At the opposite side walls (at the outlet and inlet sides for a liquid of measuring object) at the resin block 5 are inserted sample flow tubes 6 formed of, for example, polytetrafluoroethylene and into other side wall is inserted a connector pin 7. The sample flow tubes 6 each are designed to be equal in a inner diameter to the response film 8 and are connected with a liquid inlet 9 and a liquid outlet 9' through couplings, for example, contraction tubes 10, Thus, the tubes 6 and 9 and 6 and 9', which are equal in inner diameter to each other, are connected, whereby the sample lines at both sides of electrode body 1 inclusive can be designed to be linear. Accordingly, the stagnation or the like of the sample is eliminated from the electrode body and both the sides thereof, and the measurement of minute sample becomes possible thanks to the electrode body of flow system.

On the other hand, the connector pin 7 is connected with a lead wire 11 of internal electrode 2. A filler 12, e.g., a transparent silicon agent, of electrical insulating property and elasticity, is filled in the space within the block 5 except for the glass electrode body 1 so that the body 1 is integral with the block 5 through the filler 12 to thereby be extremely raised of its impact resistance. In addition, the block side walls, into which the sample flow tubes 6 are inserted, are provided at one wall with a recess 13 and at the other with a projection 14, the recess 13 and projection 14 serving to connect the shown glass electrode (whose body is incorporated with the block) in series with other electrodes (for example, reference electrode or temperature compensation electrodes) of the same size as the above. In addition, in FIG. 3, reference numeral 15 designates an O-ring.

In order to assemble the glass electrode, the following steps are preferable. At first, the glass electrode body 1 sealed with the packing 4 is housed within the box of resin block 5, the sample flow tubes 6 are connected with the liquid inlet 9 and liquid outlet 9' through couplings 10 respectively, and the lead wire 11 of internal electrode 2 is connected with the connector pin 7. Therefore, the filler is filled into the box of block and the lid closes the box.

While a preferred embodiment of the invention has been described using specific terms, such description is for illustrative purpose only, and it is to be understood that the changes and variations may be made without departing from the spirit or scope of the following claims.

We claim:

1. A flow system glass electrode characterized in that the flow system glass electrode body, which is provided with a response film along an internal flow conduit and seals an internal electrode and an internal liquid by a packing, is contained in a resin block, sample flow tubes each equal in an inner diameter to said response film and at the entrance and exit sides are inserted into the walls of said resin walls respectively, said sample flow tubes are connected with a liquid inlet and a liquid outlet at the glass electrode body side by use of couplings respectively, and a space within said resin block except for said glass electrode body is filled with a filler of electrical insulating property.

2. A flow system glass electrode according to claim 1, characterized in that said sample flow tubes are formed of polytetrafluoroethylene respectively.

3. A flow system glass electrode according to claim 2, characterized in that said glass electrode body, resin block, sample flow tubes, couplings and filler, are all transparent.

* * * * *